| United States Patent [19] | [11] Patent Number: 4,540,575 |
|---|---|
| Monaghan et al. | [45] Date of Patent: Sep. 10, 1985 |

[54] CHOLINE OXIDASE INHIBITOR

[75] Inventors: Richard L. Monaghan, Somerset; Yu-Lin Kong, Edison, both of N.J.

[73] Assignee: Merck & Co., Inc., Rahway, N.J.

[21] Appl. No.: 492,272

[22] Filed: May 6, 1983

[51] Int. Cl.³ .................. A61K 35/74; C12P 1/06
[52] U.S. Cl. .................................. 424/115; 435/169
[58] Field of Search ...................... 424/115; 435/169

Primary Examiner—Jerome D. Goldberg
Attorney, Agent, or Firm—William H. Nicholson; Mario A. Monaco

[57] ABSTRACT

New fermentation products useful in the treatment of tardive dyskinesia by inhibition of choline oxidase are produced by fermentation of a nutrient medium with a microorganism, *Streptomyces hygroscopicus.*

6 Claims, 2 Drawing Figures

CHOLINE OXIDASE INHIBITOR

SUMMARY OF THE INVENTION

This invention is concerned with fermentation products that are choline oxidase inhibitors and hence useful in the treatment of tardive dyskinesia, a disease induced by long term therapy with antipsychotic agents and marked by oral and other facial grimaces, tongue movements and torticollis.

In addition the compounds demonstrate antifungal activity against *Candida albicans, Candida krusei,* and *Candida tropicalis.*

The fermentation products are produced by fermentation of a nutrient medium with *Streptomyces hygroscopicus* and are characterized by high performance liquid chromatography, ultraviolet spectra and NMR spectra.

BACKGROUND OF THE INVENTION

Tardive dyskinesia results from long-term therapy with antipsychotic agents particularly the phenothiazines and sometimes is successfully treated with deanol (dimethylaminoethanol salt of acetamidobenzoic acid), a precursor for acetylcholine. Now, with the present invention there are provided fermentation products which are choline oxidase inhibitors useful in the treatment of tardive dyskinesia. The novel products also have antifungal activity.

There are also provided by this invention a novel fermentation process for production of the novel substance;

a novel strain of *Streptomyces hygroscopicus* used in the fermentation;

a novel process for isolation of the novel products from the fermentation broths;

novel pharmaceutical formulations containing the novel products as active ingredient;

a novel method of treatment of tardive dyskinesia by administration of an effective amount of the novel products to a patient in need of such treatment;

novel antifungal formulations; and a novel method of treatment of fungal infestation.

DETAILED DESCRIPTION OF THE INVENTION

Figure 1:
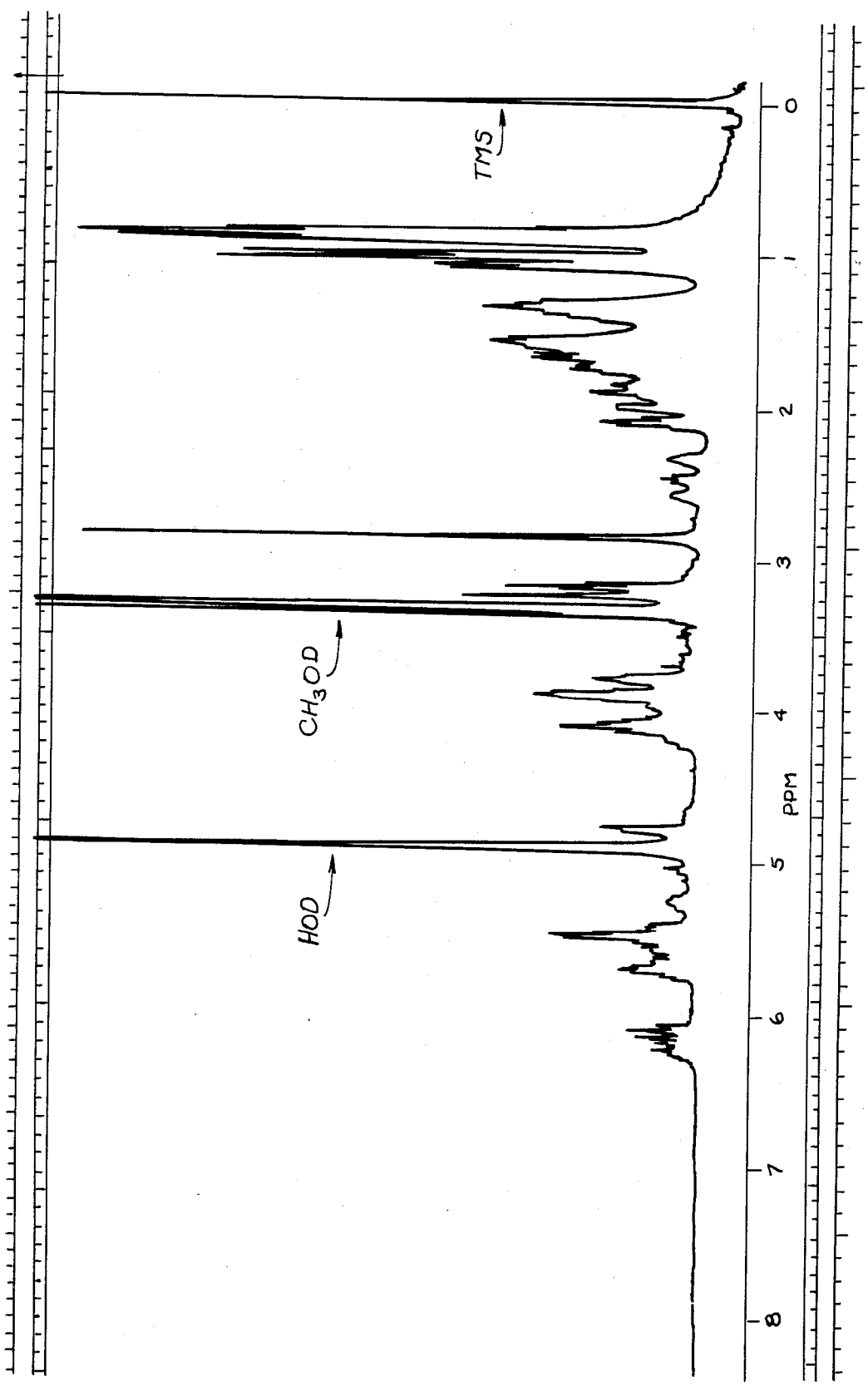

The novel fermentation process of this invention is carried out in aqueous media such as those employed for the production of other fermentation products. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, ryes, cornstarch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include for example, yeast hydolysates, primary yeast, soybean meal, cottonseed flour, hydrolysates of casein, corn steep liquor, distiller's solubles or tomatoe paste and the like. The sources of nitrogen either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the Examples are merely illustrative of the wide variety of media which may be employed, and yet are not intended to be limitative. Specifically, the carbon sources used in the culture media to produce the novel substance of this invention included dextrose, dextrin, oat flour, oatmeal, molasses, citrate, soybean oil, glycerol, malt extract, cod liver oil, starch, ethanol, figs, sodium ascorbate and lard oil. Included as nitrogen sources were peptonized milk, autolyzed yeast, yeast RNA, tomato paste, casein, primary yeast, peanut meal, distiller's solubles, corn steep liquor, soybean meal, corn meal, NZ amine, beef extract, asparagine, cottonseed meal and ammonium sulfate. The major ionic components were $CaCO_3$, $KH_2PO_4$, $MgSO_4.7H_2O$ and $NaCl$ and small amounts of $CoCl_2.6H_2O$ and traces of Fe, Mn, Mo, B and Cu were also present.

The fermentation is carried out at temperatures ranging from about 20° to 37° C.; however, for optimum results it is preferable to conduct the fermentation at temperatures of from about 22° to 30° C. The pH of the nutrient media suitable for growing the culture can vary from about 6.0 to 8.0.

Although the novel compound is produced by both surface and submerged culture, it is preferred to carry out the fermentation in the submerged state. A small scale fermentation is conveniently carried out by inoculating a suitable nutrient medium with the culture and, after transfer to a production medium permitting the fermentation to proceed at a constant temperature of about 28° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for 2 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 28° C.

The novel fermentation products of this invention are isolated from the fermentation broth by separating the broth from the mycelia by centrifugation or filtration; concentration of the filtrate activity by absorption on a macroreticular polymeric absorbent such as Amberlite XAD-2 or XAD-4, DUOLITE ES 863, or Diaion HP-20, followed by fractional elution with methanol/water mixtures; extraction of the appropriate fraction or fractions with an organic solvent such as ethyl acetate, propyl acetate, or butyl acetate, the extracts being discarded; chromatography of the extract fraction on silica gel; reverse phase high performance liquid chromatography; and concentration to dryness.

The above process results in two products each represented by a separate HPLC peak.

The product in peak 1 had the following characteristics:

U.V. Spectrum in Methanol:

| max. | $E^{1\%}$ |
| --- | --- |
| 229 nm (sh) | 262 |
| 235 nm | 275 |
| 240 nm (sh) | 188 |

$^1$H NMR Spectrum: The spectrum was recorded in CD$_3$OD (~5 mg/0.4 mL). Chemical shifts are shown in FIG. 1 in ppm relative to internal tetramethylsilane at zero ppm.

The product in peak 2 had the following characteristics:

U.V. Spectrum in Methanol:

| max. | $E^{1\%}$ |
| --- | --- |
| 229 nm (sh) | 200 |
| 235 nm | 275 |
| 240 nm (sh) | 188 |

Figure 2:
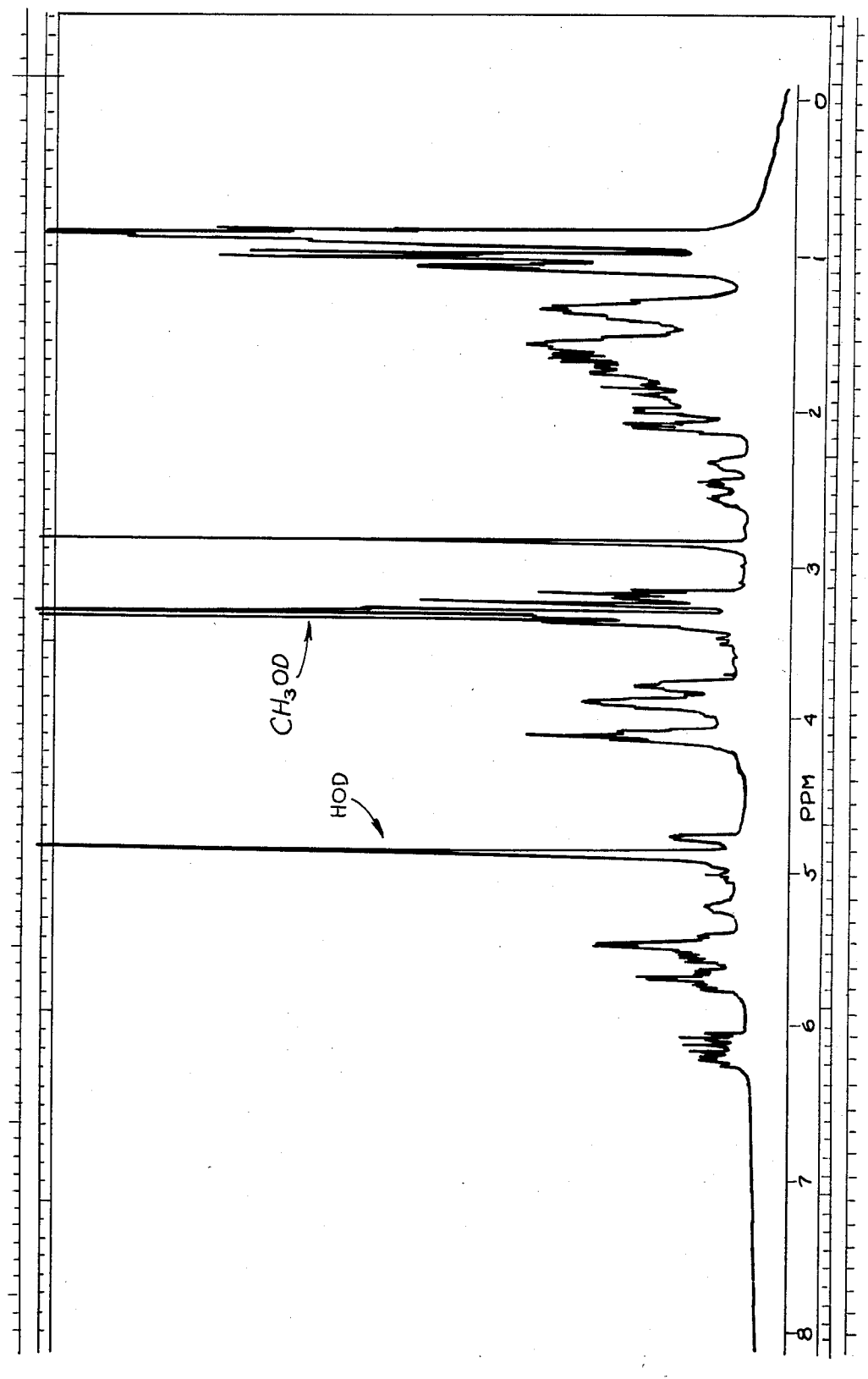

$^1$H NMR Spectrum: The spectrum was recorded in CD$_3$OD (~5 mg/0.4 mL). Chemical shifts are shown in FIG. 2 in ppm relative to internal tetramethylsilane at zero ppm.

The novel microorganism of this invention was compared with the culture descriptions in the following standard reference texts: Bergey's *Manual of Determinative Bacteriology*, 8th Ed., 1974, Williams & Wilkins Co.; Waksman, S. A., *The Actinomycetes*, Vol. II, 1961, Williams & Wilkins Co.; International Journal of Systematic Bacteriology, 18, 68–189, 1968; 18, 279–392, 1968; 19, 391–512, 1969; 22, 265–394, 1972 and it was determined to be a strain of *Streptomyces hygroscopicus*. It has been designated MA-5277 in the culture collection of Merck & Co., Inc., Rahway, N.J. and has been placed on permanent deposit with the American Type Culture Collection, 12301 Parklawn Drive, Rockville, Md 20852, and has been assigned accession No. ATCC 39296. Although the use of this particular strain is described in connection with the process of this invention, other strains of *Streptomyces hygroscopicus* including mutants are also capable of producing the novel products of this invention.

MORPHOLOGICAL AND CULTURAL CHARACTERISTICS OF *Streptomyces hygroscopicus* ATCC 39296 (V=vegetative growth; A=aerial mycelium; SP=soluble pigments; Rev.=Reverse)

Morphology: Sporophores form compact spirals, clustering along aerial hyphae. As the culture ages, spirals coalesce to become dark moist areas. Spore surface (electron microscope) smooth, with many having an irregular, roughened, almost warty appearance.

Oatmeal agar (ISP Medium 3)
  V: Rev.—brown edged with gray
  A: Gray mixed with white; entire surface becoming moist and black with age
  SP: None
Czapek Dox agar (sucrose nitrate agar)
  V: Rev.—gray
  A: Dark gray mixed with light gray and white-black moist spots appear after 14–21 days in incubation
  SP: None
Egg albumin agar
  V: Rev.—lt. brown edged with gray
  A: Gray mixed with white; moist black areas form as culture ages
  SP: None
Glycerol asparagine agar (ISP Medium 5)
  V: Rev.—brownish-tan edged with black
  A: Gray mixed with white, becoming black and moist with age
  SP: None
Inorganic salts-starch agar (ISP Medium 4)
  V: Rev.—gray edged with black
  A: Dark gray with entire surface becoming moist and black with age
SP: None
Yeast extract-malt extract agar (ISP Medium 2)
  V: Rev.—brown edged with black
  A: Dark gray mixed with brownish gray, becoming moist and black with age
  SP: None
Peptone-iron-yeast extract agar
  V: Tan
  A: None
  SP: None
  Melanin: Negative
Tyrosine Agar (ISP Medium 7)
  V: Rev. - Brown edged with black
  A: Gray becoming black and moist
  SP: Light brown
Carbon utilization
  Pridham-Gottlieb basal medium +1% carbon source;
  + =growth;
  ± =growth poor or questionable;
  − =no growth as compared to negative control (no carbon source).

| Glucose | + |
| --- | --- |
| Arabinose | ± |
| Cellulose | − |
| Fructose | + |
| Inositol | + |
| Lactose | + |
| Maltose | + |
| Mannitol | + |
| Mannose | + |
| Raffinose | ± |
| Rhamnose | + |
| Sucrose | ± |
| Xylose | ± |

Temperature range (Yeast extract-dextrose+salts agar)
  28° C.—good growth with sporulation 37° C.—good vetagive growth, no aerial
50° C.—no growth
Oxygen requirement (Stab culture in yeast extract-dextrose+salts agar)
Aerobic All readings taken after three weeks at 28° C. unless noted otherwise. pH of all media approximately neutral (6.8–7.2)

Another embodiment of this invention is a pharmaceutical formulation comprising the novel fermentation product or products as active ingredient. It may be in any art recognized form suitable for oral use, such as tablets, troches, lozenges, aqueous or oil suspensions, dispersible powders, or granules, emulsions, hard or soft capsules, syrups, or elixirs. For intravenous, intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg, and preferably from 5 to 250 mg.

A further embodiment of this invention is the treatment of tardive dyskinesia with the novel substance. The route of administration can be oral, rectal, intravenous, intramuscular, intraperitoneal or subcutaneous.

Doses of 0.1 to 20 mg/kg/day and preferably of 0.5 to 10 mg/kg/day of active ingredient are adequate, and if preferred it can be administered in divided doses given two to four times daily.

The fermentation products of this invention also have useful antifungal activities. For example they may be used to control strains of *Candida albicans, Candida krusei,* and *Candida tropicalis.* For use in controlling these microorganisms, the novel fermentation product or products are admixed with suitable formulating agents, powders, emulsifying agents or solvents such as aqueous ethanol and sprayed or dusted on the objects to be protected.

The novel fermentation products of this invention are also useful for controlling or curing infections with the same fungi in warm-blooded animals including humans by administration by the same routes and in the same dose levels as shown above for treating tardive dyskinesia.

EXAMPLE 1

Fermentation

A tube of lyophilized culture ATCC 39296 was opened aseptically and the contents suspended in 54 ml of KE seed medium in a 250 ml baffled Erlenmeyer flask. The seed medium was agitated at 28° C. on a 220 rpm shaker until heavy growth was obtained. The contents of the seed flask was used to inoculate (2.2 ml each) LR and JU production media (44 ml in a 250 ml unbaffled Erlenmeyer flask). These media were incubated for 4 days at 28° C. with agitation (220 rpm) before harvesting.

Similar fermentations were conducted in other production media, namely KA, KR and KH with similar results. Optimum production occurred in KR medium after 3 days incubation at 28° C.

|  | Gs/liter |
|---|---|
| KA Medium | |
| Dextrin (CPC modified starch) | 25.0 |
| Sodium citrate | 2.0 |
| Blackstrap molasses | 5.0 |
| Primary yeast | 5.0 |
| Soy bean meal | 15.0 |
| Corn steep liquor | 10.0 |
| NaCl | 2.5 |
| Soy bean oil | 5.0 ml |
| Distilled water | to 1000 ml |
| Adjust pH to 7.0 with NaOH | |
| $CaCO_3$ | 2.0 g. |
| KE Medium | |
| Dextrose | 1.0 |
| Soluble starch | 10.0 |
| Beef Extract | 3.0 |
| Ardamine pH | 5.0 |
| N.Z. amine, type E | 5.0 |
| $MgSO_4.7H_2O$ | 0.05 |
| Phosphate buffer | 2.0 ml |
| Distilled water | to 1000 ml |
| Adjust pH to 7.0 with NaOH | |
| $CaCO_3$ | 0.5 |
| Phosphate buffer | |
| 91 g/liter $KH_2PO_4$ | |
| 95 g/liter $Na_2HPO_4$ | |
| KH Medium | |
| Tomato paste | 20.0 |
| Primary yeast | 10.0 |
| Dextrin (CPC modified starch) | 20.0 |
| $CoCl_2.6H_2O$ | 0.005 |
| Distilled water | to 1000 mls |
| Adjust pH to 7.2–7.4 | |
| KR Medium | |
| Dextrin (CPC modified starch) | 40.0 |
| Distiller's solubles | 7.0 |
| Yeast Extract | 5.0 |
| $CoCl_2.6H_2O$ | 0.05 |
| Distilled water | to 1000 ml |
| Adjust pH to 7.3 | |
| LR Medium | |
| Glycerol | 4.0 ml |
| Dextrose | 2.0 |
| Malt Extract | 6.0 |
| Corn Steep Liquor | 16.0 ml |
| Pharmamedia | 4.0 |
| Cod Liver Oil | 1.0 ml |
| Ardamine, pH | 0.4 |
| Humic acid | 0.08 |
| Distilled Water | to 1000 ml |
| Adjust pH to 7.0 | |
| JU Medium | |
| Tomato Paste | 40 |
| Oat Flour | 15 |
| Distilled Water | to 1000 ml |
| Adjust pH to 6.0 | |

EXAMPLE 2

Using the procedures substantially as described in Example 1 a production batch of product was produced as follows:

Step A: Fermentation

1. "A" Stage: Culture MA5277, "b" (ATCC 39296) lyophilization series, is maintained in the lyophilized state in a 1.0 ml ampule containing 0.15 mls of a skim milk suspension of the culture.
2. "B" Stage
   Vessel: 250 ml 3 baffled Erlenmeyer flask containing 50 mls medium per flask.
   Medium: KE

| | Wt/Vol |
|---|---|
| Dextrose | 0.1% |
| Soluble Starch | 1.0% |
| Beef Extract | 0.3% |
| Ardamine pH | 0.5% |
| NZ-Amine Type E | 0.5% |
| $MgSO_4 \cdot 7 H_2O$ | 0.005% |
| 1.34 M Phosphate Buffer | 0.02% Vol/Vol |
| $CaCO_3$ (After pH Adjustment) | 0.05% |
| Phosphate Buffer | |
| $KH_2PO_4$ | 9.1% |
| $Na_2HPO_4$ | 9.5% |

Inoculum: Contents of one Lyo tube into each "B" flask
Incubation: 24 hours @ 28° C. on a rotary shaker with a 2" throw rotating at 220 RPM.
Sterility: Streak plates and gram stain 3. "C" Stage
   Vessel: 2 liter 3 baffled Erlenmeyer flask containing 500 mls medium
   Medium: Same as "B" stage
   Inoculum: 10 mls from "B" stage
   Incubation: Same as "B" stage
   Sterility: Same as "B" stage 4. "E" Stage (PRODUCTION)
   Vessel: 756 liter stainless steel fermentor containing 500 liters of medium
   Medium:

| Material | g/l |
|---|---|
| Modified Cornstarch | 40.0 |
| Distiller's Solubles | 7.0 |
| Yeast Extract | 5.0 |
| $CoCl_2$ | 0.05 |
| Polyglycol 2000 | 1.0 |
| Pre-Sterile pH | 7.3 |

Fermentor Volume: 501 liters
Sterilization: 20 minutes at 121° C.
Inoculum: 1 liter "C" stage
Temperature: 28° C.
Air Flow: 10 CFM
Agitation: 130 RPM
Pressure: 13 PSI
Cycle Time: 100 hours
Sterility: Microscopic examination and YED streak plates at 28° C. and 37° C.

Step B: Isolation of L-681,229 from 110 gallons of Whole Broth

1. Filtration of the Whole Broth

The whole broth (110 gals.) was filtered through a filter press using a Celite admixture. The choline oxidase inhibitory activity was found both in the filtrate and in the cells. The two were processed separately in the following manner.

2. Processing of the Filtrate (XAD-2 Chromatography)

The filtered broth was passed over a 8 gal. column of XAD-2 resin at the rate of 0.8 gal. per minute. The column was washed with 8 gal. of water and then eluted in the following manner:

| | Eluting Agent |
|---|---|
| Fraction 1 | 8 gal. $CH_3OH:H_2O::1:4$ |
| Fraction 2 | 8 gal. $CH_3OH:H_2O::3:2$ |
| Fraction 3 | 24 gal. $CH_3OH$ |

3. Extraction of the Cells and XAD-2 Chromatography of the Cell Extract

The cells were slurried in acetone: water:3:2 and stirred for one-hour.

The mixture was filtered through a Celite pad and the filtrate freed of acetone by vacuum distillation. The resulting aqueous mixture was passed over a 8 gal. column of XAD-2 resin at the rate of 0.8 gal. per min. and eluted in a fashion identical to that used for the filtered broth.

4. Pooling of the XAD-2 Active Fractions

The activity was found only in the Fraction 3 eluates of the XAD-2 chromatographies of both the filtered broth and cell extract. These active fractions were combined and concentrated to one gallon. One gallon of ethyl acetate and 2 gal. of water were added and after thorough mixing, the layers were separated. The lower aqueous methanol layer was extracted two more times with ethyl acetate as before. The ethyl acetate extracts were discarded and the aqueous methanol layer evaporated to dryness (bath temperature 45° C.). The residue was dried by co-distillation (2X) with absolute ethanol and the dried residue was dissolved in methanol.

5. Silica Gel Chromatography

The final methanol solution from Step 4 was mixed with silica gel (Mallinckrodt Silicar CC-7) and evaporated on a rotary evaporator to yield a dry free-flowing powder.

This powder was placed on top of a silica gel column (4 liters, silicar CC-7) formed in acetone. The column was then elute dusing a stepwise methanol-acetone gradient in the following manner:

| Fraction No. | Eluant |
|---|---|
| 1 | 4 l acetone |
| 2 | 4 l 5% methanol-acetone (V/V) |
| 3 | 4 l 10% methanol-acetone (V/V) |
| 4 | 4 l 20% methanol-acetone (V/V) |
| 5 | 4 l 40% methanol-acetone (V/V) |
| 6 | 4 l 60% methanol-acetone (V/V) |
| 7 | 4 l 80% methanol-acetone (V/V) |
| 8 | 4 l methanol |

The choline oxidase inhibitory activity appeared mainly in fractions 5 and 6. These fractions were pooled and used for the reverse-phase chromatography described below.

6. Reverse-Phase Chromatography

The active fractions from Step 5 were evaporated to dryness and dissolved in methanol (17 g solutes/172 ml solution). This solution was applied to a 2 l reverse-phase column packed with LiChroprep $_{TM}$ RP-18 (particle size 25–40 μm, EM Reagents) and equilibrated with 40% (V/V) methanol-water. The column was eluted with a stepwise methanol-water gradient in the following manner.

| Eluting Agent | | |
|---|---|---|
| 40% | $MeOH-H_2O$ (V/V) | (2000 ml) |
| 60% | $MeOH-H_2O$ (V/V) | (2000 ml) |
| 70% | $MeOH-H_2O$ (V/V) | (2000 ml) |

| Eluting Agent | |
|---|---|
| 80% MeOH—H₂O (V/V) | (5000 ml in all; 500 ml fractions were collected). |

The bulk of the choline oxidase inhibitory activity emerged during the elution with 80% MeOH—H$_2$O between 2800–3800 ml of eluant. There were 3.3 grams of solute in this portion of eluate.

When analyzed by high performance liquid chromatography (Zorbax-ODS, 4.6 min. ×25 cm; mobile phase, 83% methanol-17% 0.01 M phosphate pH 6.5; UV detector at 240 nm; flow rate 2.0 ml/min.), two major peaks were observed in the material from Step 6. Using the above HPLC conditions, peak 1 eluted in six minutes and peak 2 eluted in 12 minutes.

7. HPLC Preparative Chromatography Isolation of Peak 1 and Peak 2

Using a preparative HPLC column, e.g. Zorbax C-18, 21.2 mm; 25 cm; and the mobile phase, methanol/water (80/20, V/V). The product from Step 6 was further resolved into the two major peaks (1 and 2) described above. A methanol solution of the product from Step 6 was injected into the preparative system and fractions were collected using an automatic fraction collector. The fractions were analyzed by analytical HPLC using the system described in Step 6. The appropriate fractions were pooled and the solvents removed on a rotary evaporator leaving a glassy residue in each case for peaks 1 and 2, with the properties previously described.

What is claimed is:

1. Product with choline oxidase inhibitory activity produced by the controlled aerobic fermentation of an aqueous nutrient medium by *Streptomyces hygroscopicus* ATCC 39296 at a temperature range of 20°–37° C. for 3–5 days at pH 6.0 to 8.0.

2. A process for producing the product of claim 1 with choline oxidase inhibitory activity which comprises cultivating *Streptomyces hygroscopicus* ATCC 39296 under controlled aerobic conditions in an aqueous nutrient medium at a temperature range of 20°–37° C. for 3–5 days at pH 6.0 to 8.0.

3. A choline oxidase inhibitory pharmaceutical formulation comprising a pharmaceutical carrier and an effective choline oxidase inhibitory amount of the product of claim 1.

4. A method of treating tardive dyskinesia which comprises the administration to a patient in need of such treatment an effective anti-tardive dyskinesia amount of the product of claim 1.

5. An antifungal pharmaceutical formulation comprising an effective antifungal amount of the product of claim 1 and a pharmaceutically acceptable carrier.

6. A method of treating a fungal infection by administration to a patient in need of such treatment of an effective antifungal amount of the product of claim 1.

* * * * *